United States Patent [19]

Moggi et al.

[11] 4,259,463

[45] Mar. 31, 1981

[54] VULCANIZABLE COMPOSITIONS BASED ON COPOLYMERS OF VINYLIDENE FLUORIDE AND CONTAINING VULCANIZATION ACCELERATORS WHICH ARE AMINOPHOSPHINIC COMPOUNDS

[75] Inventors: Giovanni Moggi, Milan; Livio Mancini, Peschiera Borromeo, both of Italy

[73] Assignee: Montedison S.p.A., Milan, Italy

[21] Appl. No.: 968,029

[22] Filed: Dec. 8, 1978

[30] Foreign Application Priority Data

Dec. 14, 1977 [IT] Italy .............................. 30688 A/77
Nov. 20, 1978 [IT] Italy .............................. 29945 A/78

[51] Int. Cl.$^3$ ..................... C08F 8/40; C08F 214/22
[52] U.S. Cl. ............................. 525/331; 260/42.27; 260/959; 428/421; 525/340; 525/350
[58] Field of Search .................. 526/247, 253, 255; 525/340, 341, 350, 331

[56] References Cited

U.S. PATENT DOCUMENTS

| | | | |
|---|---|---|---|
| 3,655,727 | 4/1972 | Patel | 526/27 X |
| 3,752,787 | 8/1973 | de Brunner | 526/27 X |
| 3,920,620 | 11/1975 | Ceccato | 526/27 X |
| 4,018,822 | 4/1977 | Sharma | 260/551 P |
| 4,027,086 | 5/1977 | Lo Valvo | 526/79 |
| 4,032,699 | 6/1977 | West | 526/18 |
| 4,062,830 | 12/1977 | Ceccato | 526/18 |

FOREIGN PATENT DOCUMENTS 459085 9/1976 U.S.S.R. ................................. 526/27

*Primary Examiner*—C. A. Henderson

[57] ABSTRACT

There are disclosed vulcanizable compositions of vinylidene fluoride copolymer elastomers comprising, in addition to the elastomeric fluoride copolymer, an inorganic acid acceptor, a basic compound, a polyhydroxy or polythiol vulcanizing agent, and an aminophosphinic compound of the class of phosphoraneamine and phosphorimidic acid triamide. The presence of the aminophosphinic compound facilitates satisfactory vulcanization rates without scorching. The vulcanized fluorinated elastomers produced therefrom may be used as gaskets for sealing purposes and as protective layers in contact with corrosive chemical agent. They are particularly useful in applications requiring strong adhesion to metallic surfaces even under severe temperature conditions.

7 Claims, No Drawings

VULCANIZABLE COMPOSITIONS BASED ON COPOLYMERS OF VINYLIDENE FLUORIDE AND CONTAINING VULCANIZATION ACCELERATORS WHICH ARE AMINOPHOSPHINIC COMPOUNDS

THE PRIOR ART

The vulcanized elastomers based on vinylidene fluoride copolymer are well known to the Prior Art and are widely used in numerous applicative fields, where exceptional resistance to chemicals and solvents, lubricants, fuels, acids and similar products is required, even at very high temperatures.

The vulcanized articles obtained from such elastomeric copolymers find their most suited application as sealing gaskets or packings in general, both in static as well as dynamic conditions, in the motor-engineering, aeronautical, missilistic, naval, mechanical, chemical field, in protective impermeabilizations of various supports such as for instance: protective garments for contact with aggressive chemical agents, sheathes for electrical cables exposed to high thermal radiation and lastly as protective coatings of industrial containers.

According to the most advanced Prior Art for the vulcanization of the elastomeric copolymers of vinylidene fluoride, as vulcanizing agents there are used polynucleophilic compounds and in particular polyhydroxylic aromatic compounds (or analogous thioderivatives), either as such or in a salified form.

These products leads, in fact, to vulcanized products of absolutely satisfying physical-mechanical characteristics and of an altogether satisfying thermal resistance.

Such products have, however, the disadvantage of requiring extremely long vulcanizing times, wherefore they are used in combination with substances having an accelerating action.

With the known vulcanizing systems, however, it is not possible to obtain a satisfactory adhesion to the metals of the vulcanized compositions, nor is it possible to carry out the injection molding of articles with short runs and in the absence of "scorching" phenomena.

Amongst the substances that develop an accelerating action according to the most advanced Prior Art, there are described derivatives of tertiary amines containing 4 (four) covalent nitrogen-carbon linkages and derivatives of tertiaryphosphines containing 4 (four) covalent phosphorous-carbon linkages (French Pat. Nos. 2,091,806 and 2,096,115).

THE PRESENT INVENTION

We have surprisingly found that some compounds containing 1 or more simple phosphorous-nitrogen linkages may be conveniently used as vulcanization accelerating agents for fluoroelastomers.

Not all the compounds containing the P-N linkage do exert an accelerating action in the vulcanization of fluoroelastomers; for instance, non-active are compounds such as phosphin-imine $(C_6H_5)_3P=N-C_6H_5$, while the corresponding isosteric phosphorane (see Brit. Pat. No. 1,413,857) $(C_6H_5)_3P=CH-R$ is described as an accelerating agent.

On the contrary, according to this invention there may be conveniently used the compounds obtained from the reaction of some tri-coordinated aminophosphinic derivatives such as for instance the reaction product between tris-dimethylamine of phosphorous acid $[(CH_3)_2N]_3P$ and alkyl halides.

There thus forms a compound whose action mechanism is still unknown but which presumably behaves as a ionic couple on the interface between an organic phase represented by the elastomer and an inorganic phase represented by charges of oxides and alkaline-earthy hydrates present in the vulcanization formula.

Thus, object of this invention is that of providing vulcanizable compositions based on elastomeric copolymers of vinylidene fluoride, containing as vulcanizing agents polynucleophilic compounds that be free of the above mentioned drawbacks.

Still another object of this invention is that of providing a vulcanizing process for compositions based on elastomeric copolymers of vinylidene fluoride free of the above mentioned drawbacks and that shall yields vulcanized products having a high degree of adhesion to metal substrates.

A third object of this invention is that of providing vulcanized compositions based on elastomeric compositions of vinylidene fluoride, and that be free of the above mentioned drawbacks and that may be prepared by injection molding.

These and still other objects may be attained with vulcanizable compositions consisting of:

(I) 100 parts by weight of an elastomeric copolymer of vinylidene fluoride, with one or more fluorinated or chloro-fluorinated monomers, ethylenically unsaturated, such as for instance: 1-hydropenta-fluoropropene, 2-hydropenta-fluoropropene, 1,1-dihydrotetrafluoropropene, hexafluoropropene, tetra-fluoroethylene, trifluorochloroethylene, alkyl- and arylvinyl ethers, partially or totally fluorinated, and the likes.

(II) 1-40 parts by weight of an acceptor of inorganic acids, consisting of one or more basic oxides of bivalent metals such as magnesium oxide, calcium oxide, lead monoxide, zinc oxide and/or at least one basic lead phosphite, possibly in the form of complexes or of cationic chelates.

(III) 0.5-10 parts by weight of one or more basic compounds such as calcium hydrate, strontium hydrate and barium hydrate, the metal salts of weak acids such as: calcium-, strontium-, barium, sodium- and potassium carbonates, benzoates and phosphates, possibly in the form of complexes with normal cationic chelating or complexing agents of the type well known to the skilled in the Art;

(IV) 0.5-15 parts by weight, but preferably 1-6 parts by weight of a vulcanizing agent based on one or more polyhydroxyl and/or polythiol compounds of general formulas:

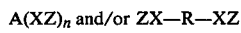

$$A(XZ)_n \text{ and/or } ZX-R-XZ$$

wherein A is an arylene radical; n is a whole number equal to or greater than 2, X is oxygen or sulphur; Z is hydrogen or an alkaline metal; R is an alkylene or cycloalkylene, mono- or polyalkylencycloalkyl, or alkylendiaryl or oxoalkylendiaryl radical;

(V) 0.05-5 parts by weight of a vulcanization accelerator based on aminophosphinic derivatives of the general formulas:

$$\underset{\underset{CR^{iv}R^{v}}{\|}}{P}(NR'R'')_qR'''_{3-q} \qquad (I)$$

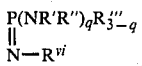

wherein:
R', R" and R'", equal to or different from each other, may be: alkyl, cycloalkyl, aryl, arylalkyl, oxyalkyl or poly-oxyalkyl groups with a free or etherified terminal OH function, containing from 1 to 18, but preferably from 1 to 12 carbon atoms and may contain, as substituents, halogens, CN, OH, carboalkoxy groups; moreover, R' and R" may be connected with each other to form with the nitrogen atom a heterocyclic ring;

q is a whole number comprised between 1 and 3;

$R^{iv}$ is hydrogen or alkyl group containing from 1 to 16 carbon atoms, or carbalkoxy group—COOR in which R is a $C_1$–$C_8$ alkyl;

$R^v$ is a carbalkoxy group—COOR in which R is a $C_1$–$C_8$ alkyl, or —CN, or —$CONH_2$, or $C_1$–$C_{16}$ alkyl, or aryl group;

$R^{iv}$ and $R^v$ may be connected with each other to form with the carbon atom a cyclic group such as for example:

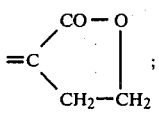

$R^{vi}$ is an aryl group, or a carbalkoxy group—COOR in which R is a $C_1$–$C_8$ alkyl, or a carbaryloxy group—COOAr in which Ar is aryl;

or of the ionic type, comprised in the formulas:

$$[P(NR'R'')_n R_{4-n}''']_m^+ \cdot Y^{m-} \quad (III)$$
$$R[P(NR'R'')_r R_{3-r}''']_2^+ \cdot pY^{m-} \quad (IV)$$

wherein:
R', R", R'", have the meanings above shown for the formulas (I) and (II);

R is a bivalent alkylenic, arylenic or oxoalkylenic radical;

n is a whole number comprised between 1 and 4;

r is a whole number comprised between 1 and 3;

m is a whole number comprised between 1 and 3, corresponding to the valence of anion Y; and m.p=2.

Anion Y of valency m may be either organic or inorganic, as halide, perchlorate, nitrate, tetrafluoroborate, hexafluophosphate, oxalate, acetate, stearate, haloacetate, p.toluensulphonate, or as OH. It may also be a complex anion such as for instance; $ZnCl_4^{--}$, $CdCl_4^{--}$, $NiBr_4^{--}$, $HgI_3^-$, $HgI_4^{--}$.

The use of the anions complexed with metal salts proves particularly convenient, in as much as these compounds may be introduced in the mix as such, without the help of vehiculating agents, usually used in the Prior Art for compounds of an ammonium salt structure which are difficult to be obtained in the solid crystalline state.

The vulcanizable compositions of the above described type, are vulcanized by means of a process, likewise object of this invention, which consists in first heating said compositions under pressure and at temperatures comprised between 130° C. and 230° C., but preferably between 160° and 200° C., for a period of from 0.5 to 60 minutes, but preferably comprised between 1 and 20 minutes; by then post-vulcanizing the manufactured articles thus obtained in an oven or furnace, at atmospheric pressure, at temperatures comprised between 130° and 315° C., but preferably between 200° C. and 275° C., for a period of between 5 and 48 hours, but preferably between 10 and 24 hours.

It has now surprisingly been found that the compositions vulcanizable according to this invention, may be transformed into manufactured articles of any shape and dimension, by extrusion forming and successive vulcanization, also using highly automatized injection molding techniques. In fact, at the usual plasticizing temperatures for injection molding no drawbacks are experienced because of scorchings or tearings under heat.

Said manufactured articles display an excellent resistance to permanent set and to compression, a minimum tendency to scorching in relationship to time and storing temperature or to the temperature of particular processing techniques, such as for instance extrusion, and they also show a high resistance to thermal ageing. Moreover, they may be coupled to metal supports or supports of alloys thereof, towards which they show an exceptional adhesion even at high temperature, for instance at 250° C. and more.

It was also noticed that the vulcanizable compositions, comprising the additives from (I) to (V) as indicated above, do not cause any phenomena of stickyness and soilability of the molds, wherefore production wastes are practically eliminated thereby allowing high production standards and extremely regular processing cycles.

The process according to this invention proves particularly indicated in the case of copolymers containing from 30 to 70 mols % of vinylidene fluoride and from 70 to 30 mols % of 1-hydro-pentafluoropropene and/or hexafluoropropane or of vinylidene fluoride/tetrafluoroethylene/hexafluoropropene (or 1 hydropentafluoropene) terpolymers, in which the percentual quantities of the three monomers are comprised respectively betwee 40 and 80, 30 and 10 and 30 and 10 mols percent.

More generally, the process according to this invention may be conveniently applied to all fluorinated polymeric materials of the elastomeric type, possibly containing substituents different from fluorine and chlorine, and also to mixtures of two or more fluorinated elastomers.

The polyhydroxylic or polythiolic compounds to be used as vulcanizing agents according to the invention, are those well known to the skilled in the Art. More particularly suited for the purpose are: hydroquinones, resorcin, catechol, naphtols, polyhydroxybenzophenones, bisphenols and derivatives thereof containing in the aromatic ring and/or in the aliphatic group (R=alkylendiarylene) substituents different from hydrogen and, in particular, halogens such as chlorine and fluorine, and corresponding thiolderivatives, both as such as well as mono, bisalified or polysalified with alkaline metals; lower aliphatic and cycloaliphatic diols such as 1,4-butandiol; di-alkylencycloaliphatic diols such as 1,4(di-hydroxymethyl)cyclohexane and dialkylenaromatic diols such as 1,4(dihydroxymetil)benzene and the corresponding derived thiols, both as such as well as mono- or bisalified with alkaline metals.

Preferred classes of products to be used according to this invention as accelerators, include compounds, of the previously cited formulas (I) and (II) in which:

R$^{iv}$ is H or —CH$_3$, R$^v$ is —COOCH$_3$ or —COOC$_2$H$_5$; R$^{vi}$ is —C$_6$H$_5$ or —C$_6$H$_4$CH$_3$;

R''' is alkylaryl as benzyl or alkyl with from 1 to 6 carbon atoms;

R' and R'' are methyl or ethyl;

q = 2 or 3 in formula (I) and 3 in formula (II).

Preferred compounds of the formulas (III) and (IV) are those in which R', R'' and R''' have the meanings above shown, Y is Cl—, Br—, I—, HgI$_4$—— or CdCl$_4$——.

Examples of compounds that are particularly suited for use in the vulcanizable composition of this invention are the following: [the names have been desumed mostly from the rules of the Chemical Abstract: of course the compounds can be represented also in ionic form according to the formulas (III) and (IV) above shown]:

{P[N(CH$_3$)$_2$]$_3$(CH$_2$C$_6$H$_5$)Cl}$_2$CdCl$_2$  or:
{P[N(CH$_3$)$_2$]$_3$(CH$_2$C$_6$H$_5$)}$_2$++. CdCl$_4$—— dichloro-bis-[1 chloro-1 benzyl-N,N'N'' hexamethyl-phosphorane-triammine]-cadmium (II); melting point = 149° C.

P[N(CH$_3$)$_2$]$_3$=NC$_6$H$_5$

N, N', N'', -hexamethyl, N''' phenyl, phosphorimidic triamide: (oil) b.p. (0,5 mm Hg) = 100° C.

was prepared as described by H. Goldwhite et al. (J. Chem. Soc. Dalton 1975, 12).

P[N(CH$_3$)$_2$]$_3$=N (o.CH$_3$C$_6$H$_4$)

N, N', N'' -hexamethyl, N''' (o.tolyl), phosphorimidic triamide: (oil), b.p. = 140° C. (0.1 mm Hg) was prepared according to I. N. Zhmurova et al. (Zh. Obshch. Khim 1968, 2078; cfr. Ch. Abstr. 70, 28999 b)

P[N(CH$_3$)$_2$]$_3$=C(CH$_3$)COOCH$_3$ b.p. = 145° C. (1.2 mm Hg)

N, N', N'' hexamethyl, -1-[(carbomethoxy) ethylidene]phosphoranetriamine (oil).

This product was prepared from 1 bromo, 1(carbomethoxy-ethyl)-N, N', N'' hexamethyl phosphorane triamine (obtained by reaction of methylester of the α-bromopropionic acid with hexamethyl phosphorous triamide in dioxane at 70° C.) with K$_2$CO$_3$ in propionitrile at reflux for 2 hr.

P[N(CH$_3$)$_2$]$_3$=CH—COOC$_2$H$_5$

N, N', N'', hexamethyl, 1-[(carbethoxy) methylene]-phosphorane triamine (oil) b.p. = 150° C. (1.5 mm Hg).

This compound was prepared as indicated above but using ethyl bromoacetate.

P[N(CH$_3$)$_2$]$_2$(C$_6$H$_5$)=C(CH$_3$)COOCH$_3$

N, N', tetramethyl, 1 phenyl, 1-[(carbomethoxy) ethylidene]phosphorane diamine, (oil) was prepared in a similar way, starting from bis (dimethylamino)phenil phosphine and methylester of the α-bromopropionic acid.

{P[N(C$_2$H$_5$)$_2$](C$_6$H$_5$)$_2$(CH$_2$C$_6$H$_5$)}+.Br—  or P[N(C$_2$H$_5$)$_2$](C$_6$H$_5$)$_2$(CH$_2$C$_6$H$_5$)Br.

1-Bromo-1,1 diphenyl-1 benzyl-N diethyl-phosphoranamine, m.p. = 242° C.

P[N(C$_2$H$_5$)$_2$](C$_6$H$_5$)$_2$(CH$_2$C$_6$H$_5$)Cl 1 chloro-1, 1 diphenyl-1 benzyl-N diethyl-phosphoranamine, m.p. = 216° C.

P[N(C$_2$H$_5$)$_2$](C$_6$H$_5$)$_2$(CH$_2$C$_6$H$_5$)BF$_4$ 1 tetrafluoroborate-1, 1 diphenyl-1 benzyl-N diethyl-phosphoranamine, m.p. = 130° C.

P[N(C$_2$H$_5$)$_2$](C$_6$H$_5$)$_2$(CH$_3$)I 1 iodo-1, 1 diphenyl-1 methyl-N diethyl-phosphoranamine, m.p. = 128° C.

P[N(C$_2$H$_5$)$_2$](C$_6$H$_5$)$_2$ (CH$_3$) I. HgI$_2$ diiodo[1 iodo-1,1 diphenyl-1 methyl-N diethyl-phosphoranamine]Mercury (II), m.p. = 116° C.

(The above listed compounds have been prepared in a similar way as that described by G. Ewart et al. (Jr. of Chem. Soc., 1962, 3984). The tetrafluoborate was prepared from the corresponding chlorine with NaBF$_4$).

CH$_2${P[N(CH$_3$)(C$_2$H$_5$)](CH$_3$)$_2$]$_2$.2ClO$_4$ bis (1 perchlorate-1, 1 dimethyl-N nethyl, N phenyl-phosphoranamine)methane.

P[N(CH$_3$)$_2$]$_2$(C$_6$H$_5$)$_2$ClO$_4$ 1 perchlorate-1, 1 diphenyl-N, N'-tetramethyl-phosphorandiamine, m.p. = 161° C.

P[N(C$_2$H$_5$)$_2$]$_2$ (C$_6$H$_5$)$_2$ ClO$_4$ 1 perchlorate-1, 1-diphenyl-N, N'-tetraethyl-phosphorandiamine, m.p. = 150° C.

The preceding compounds have been prepared as described by R. Appel and R. Milker (Ber., 108, 249 (1975)). On the contrary, operating as described by R. F. Hudson et al. (Helv. Ch. Acta, 47, 632) (1964), the following compounds were prepared:

P[N(CH$_3$)$_2$]$_2$(C$_6$H$_5$)(C$_6$H$_5$CH$_2$)Br 1 bromo-1 phenyl-1 benzyl-N, N'-tetramethyl-phosphorandiamine, m.p. = 179° C.

P[N(CH$_3$)$_2$]$_2$(C$_6$H$_5$)(C$_6$H$_5$CH$_2$)Cl 1 chloro-1 phenyl-1 benzyl-N,N'-tetramethyl-phosphorandiamine, m.p. = 180° C.

P[N(C$_2$H$_5$)$_2$]$_2$(C$_6$H$_5$)(C$_6$H$_5$CH$_2$)Br 1 bromo-1 phenyl -1 benzyl-N,N'-tetraethyl-phosphorandiamine, m.p. = 164° C.

P[N(C$_2$H$_5$)$_2$]$_2$(C$_6$H$_5$)(C$_6$H$_5$CH$_2$)Cl 1 chloro-1 phenyl-1 benzyl-N,N'-tetraethyl-phosphorandiamine, m.p. = 135° C.

P[N(C$_2$H$_5$)$_2$]$_2$ (C$_6$H$_5$)(C$_6$H$_5$CH$_2$)BF$_4$ 1 tetrafluoborate-1 phenyl-1 benzyl-N,N'-tetraethyl-phosphorandiamine, m.p. = 75° C.

(prepared from the corresponding chloride with NaBF$_4$)

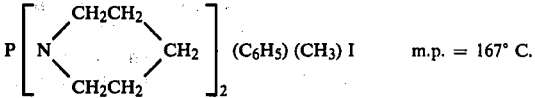

prepared according to Michaelis et al. Ber. 31, 1044 (1898).

Lastly, according to G. Ewart et al., (loc. cit.) the following compounds were prepared:

P[N(CH$_3$)$_2$]$_2$(C$_6$H$_5$)(CH$_3$) J.HgI$_2$ diiodo[1 iodo-1 phenyl-1 methyl-N,N'tetramethyl-phosphorandiamine]Mercury (II), m.p. = 133° C.

{P[N(CH$_3$)$_2$]$_2$ (C$_6$H$_5$)(CH$_3$)I}$_2$HgI$_2$

Diiodo bis[1 iodo-1 phenyl-1 methyl-N,N' tetramethyl-phosphorandiamine]Mercury (II), m.p. = 78° C.

{P[N(CH$_3$)(C$_2$H$_5$)]$_2$(C$_6$H$_5$)(CH$_3$)I}$_2$HgI$_2$ diiodo bis[1 iodo-1 phenyl-1 methyl-N,N']dimethyl-diethyl-phosphorandiamine]Mercury (II), m.p. = 159° C.

From amongst the compounds of phosphorantrialine we may list:

P[N(CH$_3$)$_2$]$_3$ (CH$_3$)I 1 iodo-1 methyl-N, N', N'' hexamethyl-phosphorantriamine, m.p. > 300° C.

prepared as described by H. Möth and H. J. Vetter [Ber. 98, 1981 (1965)]

P[N(CH$_3$)$_2$]$_3$(CH$_2$C$_6$H$_5$)Cl
1 chloro-1 benzyl-N,N',N''-hexamethyl-phosphorantriamine, m.p.=208° C.

P[N(CH$_3$)$_2$]$_3$2-ClC$_6$H$_4$CH$_2$)Cl
1 chloro-1 (o.chlorobenzyl)-N,N',N'' hexamethyl-phosphorantriamine, m.p.=232° C.

P[N(C$_2$H$_5$)$_2$]$_3$ (3,4-Cl$_2$-C$_6$H$_3$CH$_2$)Cl
1 chloro-1 (m.p. dichlorobenzyl)-N,N'N''hexamethyl-phosphorantriamine, m.p.=144° C.

prepared as described in U.S. Pat. No. 2,703,814 in the name of MONSANTO Chemical Company.

By the same method there were prepared the following compounds:

P[N(C$_2$H$_5$)$_2$]$_3$ (C$_6$H$_5$CH$_2$) Cl
1 chloro-1 benzyl-N,N'N'' hexaethyl-phosphorantriamine, m.p.=105° C.

P[N(C$_2$H$_5$)$_2$]$_3$ (C$_6$H$_5$CH$_2$) Br
1 bromo-1 benzyl-N,N'N'' hexaethyl-phosphorantriamine, m.p.=98° C.

P[N(C$_2$H$_5$)$_2$]$_3$ (C$_6$H$_5$CH$_2$) PF$_6$
1 hexafluorophosphate-1 benzyl-N,N'N'' hexaethyl-phosphorantriamine m.p.=113° C.

prepared from the corresponding chloride by the action of HPF$_6$.

P[N(C$_2$H$_5$)$_2$]$_3$ (CH$_3$) I
1 iodo-1 methyl-N,N'N'' hexaethyl-phosphorantriamine, m.p.=52° C.

The tetraamino-substituted compound: P[N(CH$_3$)$_2$]$_4$.I
1-iodo-N,N',N'', N''' octamethyl-phosphorantetraamine, m.p. >300° C.

was prepared according to the method described by P. Haasemann and J. Goubean in 'Zeitung der Anorganischen Allgemeinen Chemie,' 408, 293–303 (1974).

The quantity of accelerating agent to be used in the process according to this invention, although they remain within the limits previously herein above indicated, depends on the solubility of the additive in the fluorinated elastomer, on the presence or absence of steric hindrances in the additive itself, on the degree of basicity of the vulcanizable composition and on many other factors bound to the other particular derivatives used, on the type, shape and dimension of the manufactured article to be prepared, on the vulcanization conditions and on the system and heating procedures during the vulcanization.

The vulcanizable compositions according to the invention may contain, in addition to the substances previously indicated in (I)–(V), carbonblack, white and coloured fillers, plasticizers and lubricants of the known type, such as: stearates, arylphosphates, polyethers, polyesters, polyethylene, and other known additives, according to the teachniques currently adopted by the users of fluorinate elastomers.

The components of the Vulcanizable compositions according to this invention are easily to incorporate into the elastomeric copolymer of the vinylidene fluoride, both separately as well as pre-mixed, or they may be solubilized in solvents and then made to be adsorbed on inert fillers having a high superficial area, without that there arises any undesirable secondary phenomenon, such as for instance superficial efflorescence caused by migration phenomena inside the vulcanizable composition.

In this way good vulcanization rates can be attained at normal processing temperatures without, however, incuring in the danger of scorchings (pre-vulcanization) in the preliminary processing stages that procede the vulcanization operation proper.

Lastly, another advantage, according to this invention, consists in the complete elimination of the undesired "flash shrinkage" in the closed pressurized vulcanizing mold on the flourinated elastomer products, in particular in the case of O-ring gaskets.

In a preferential form of embodiment of the process object of this invention, the mixture of the amino-phosphonic compound or its metal complex (0.1–1 parts by weight) and the vulcanizing agent (1–6 parts by weight) is additioned in the fluorinated elastomer (100 parts by weight), before the addition of the acid acceptor (2–10 parts by weight), with the basic compounds (1–7 parts by weight), with the reinforcing and inert fillers, lubricants, plasticizers and with other possible additives.

Operating in this way, one achieves a fast, controlled and uniform vulcanization, without the danger of the appearance of undesired phenomena such as, for instance, scorchings during the various processing stages of the mix or during its storage. Similarly, any danger of losses due to volatilization during preparation and preservation of the vulcanizable compositions, is avoided, while, moreover, no special precautions are required on the part of the personnel in charge of the processing operations.

The fluorinated elastomers obtained from the compositions according to the invention, may be employed as sealing gaskets, for static or dynamical tightness, as gaskets in the motor-engineering, mechanical and naval-engineering fields, as protective wear or clothes against the contact with aggresive chemical agents, as protective sheathes for electrical cables when exposed to intensive thermal radiation, as well as in other analogous applications.

The examples that follow hereunder are given for purely illustrative purposes and are not to be taken in any way as of a limiting character.

EXAMPLE 1

Following the previously described techniques, there were prepared the following compounds:
A$_1$=P[N(C$_2$H$_5$)$_2$](C$_6$H$_5$)$_2$(C$_6$H$_5$CH$_2$) Br
A$_2$=P[N(C$_2$H$_5$)$_2$]$_2$ (C$_6$H$_5$) (CH$_3$) I
A$_3$=P[N(CH$_3$)$_2$]$_3$ (CH$_3$) I
A$_4$=P[N(CH$_3$)$_2$]$_3$ (C$_6$H$_5$CH$_2$) Br
A$_{12}$=P[N(CH$_3$)$_2$]$_3$=NC$_6$H$_5$
A$_{13}$=P[N(CH$_3$)$_2$]$_3$=N(o.CH$_3$)C$_6$H$_4$
A$_{14}$=P[N(CH$_3$)$_2$]$_3$=C(CH$_3$)COOCH$_3$
A$_{15}$=P[N(CH$_3$)$_2$]$_2$ (C$_6$H$_5$)=C(CH$_3$)COOCH$_3$ Said compounds were used as components of vulcanizable compositions of elastomeric copolymers or their alkaline mono-salts, as vulcanizing agents.

To this purpose there were used mixes consisting of 100 parts by weight of a fluorinated elastomer of the type known on the market under the name of Tecnoflon NM (trade mark of Montedison S.p.A. and concerning an elastomeric copolymer of vinylidene fluoride with hexafluoropropene in a molar ratio of 4:1, having a Mooney ML (1+4) viscosity at 100° C.=75, and with a specific weight at 25° C. of 1.816 g/cm$^3$. ), 5 parts by weight of magnesium oxide having a high surface activity, 30 parts by weight of carbonblack MT and 8 parts by weight of Ca(OH)$_2$.

The compound of the previously indicated type was admixed to the vulcanizing agent and subsequently incorporated into the raw elastomer in a roller mixer (roller mill) cooled by water circulation, before adding the other components of the mix.

In this way there were prepared 8 mixes that were then subjected to vulcanization at 185° C. for 12 minutes, under pressure. Thereupon, the mixes were subjected to post-vulcanization in an air circulation and exchange over at 250° C., for 20 hours, with a gradual growth of the temperature from 100° C. to 250° C. in 5 hours.

In the following Table 1 there have been recorded the data relating to the qualitative-quantitative composition of the mixes under examination and with regard to the characteristics of the vulcanized articles therefrom obtained.

TABLE 1

| FORMULATIONS n° | 1 | 2 | 3 | 4 |
|---|---|---|---|---|
| Tecnoflon NM parts. b.w. | 100 | 100 | 100 | 100 |
| Mgφ(Maglite D) parts b.w. | 3 | 3 | 3 | 3 |
| Ca(OH)$_2$ parts b.w. | 7 | 7 | 7 | 7 |
| Carbonblack MT parts b.w. | 30 | 30 | 30 | 30 |
| Hydroquinone parts b.w. | 1,2 | 1,2 | 1,2 | 1,2 |
| Accelerator: A$_1$ millimols | 1 | — | — | — |
| Accelerator: A$_2$ millimols | — | 1 | — | — |
| Accelerator: A$_3$ millimols | — | — | 1 | — |
| Accelerator: A$_4$ millimols | — | — | — | 1 |
| Thermo-mechanical charact. | | | | |
| O.D.R. 170° C.[1] | | | | |
| Torque inch/lbs: | | | | |
| after minutes: 2.5 | 11 | 20 | 16 | 19 |
| after minutes: 5 | 37 | 49 | 34 | 24 |
| after minutes: 7.5 | 64 | 65 | 49 | 60 |
| after minutes: 10 | 77 | 89 | 60 | 73 |
| after minutes: 15 | 91 | 93 | 82 | 86 |
| after minutes: 20 | 98 | 95 | 97 | 94 |
| after minutes: 30 | 103 | 98 | 106 | 96 |
| Viscosity | | | | |
| Mooney MS at 121° C.[2] | | | | |
| minimum | 50 | 48 | 52 | 51 |
| minutes for increase of 10 points | 40 | 56 | +2 points after 60 minutes | 46 |
| Vulcanization | | | | |
| press 170° C. × 10 min. | | | | |
| oven 250° C. × 16 hrs. | | | | |
| elst. modulus at 100% of elongation kg/sq. cm[3] | 65 | 70 | 85 | 75 |
| breaking load kg/sq/cm[3] | 160 | 155 | 140 | 150 |
| elongation at break in %[3] | 190 | 185 | 200 | 205 |
| hardness IRHD[4] | 73 | 75 | 70 | 75 |
| Compression set, on O-rings (φ 25,4 × 3,53 mm):[5] | | | | |
| at 200° C. × 70 hours | 21 | 19 | 20 | 19 |
| at 200° C. × 168 hours | 30 | 30 | 31 | 28 |

| FORMULATIONS n° | 5 | 6 | 7 | 8 |
|---|---|---|---|---|
| Tecnoflon NM parts b.w. | 100 | 100 | 100 | 100 |
| Mgφ(Maglite D) parts b.w. | 3 | 3 | 3 | 3 |
| Ca(OH)$_2$ parts b.w. | 7 | 7 | 7 | 7 |
| Carbonblack MT parts b.w. | 30 | 30 | 30 | 30 |
| Hydroquinone parts b.w. | 1,2 | 1,2 | 1,2 | 1,2 |
| Accelerator: A$_{12}$ millimols | 1 | — | — | — |
| Accelerator: A$_{13}$ millimols | — | 1 | — | — |
| Accelerator: A$_{14}$ millimols | — | — | 1 | — |
| Accelerator: A$_{15}$ millimols | — | — | — | 1 |
| Thermo-mechanical charact. | | | | |
| O.D.R. 170° C.[1] | | | | |
| Torque inch/lbs: | | | | |
| after minutes: 2.5 | 19 | 14 | 10 | 12 |
| after minutes: 5 | 47 | 36 | 35 | 45 |
| after minutes: 7.5 | 62 | 48 | 60 | 66 |
| after minutes: 10 | 86 | 57 | 75 | 90 |
| after minutes: 15 | 91 | 85 | 90 | 94 |
| after minutes: 20 | 93 | 96 | 96 | 96 |
| after minutes: 30 | 96 | 101 | 100 | 98 |
| Viscosity | | | | |
| Mooney MS at 121° C.[2] | | | | |
| minimum | 50 | 47 | 51 | 52 |
| minutes for increase of 10 points | 44 | 55 | 42 | 58 |
| Vulcanization | | | | |
| press 170° C. × 10 min. | | | | |
| oven 250° C. × 16 hrs. | | | | |
| elst. modulus at 100% of elongation kg/sq.cm[3] | 65 | 80 | 75 | 75 |
| breaking load kg/sq/cm[3] | 155 | 150 | 145 | 155 |

TABLE 1-continued

| | | | | |
|---|---|---|---|---|
| elongation at break in %[3] | 185 | 195 | 200 | 195 |
| hardness, IRHD[4] | 70 | 75 | 70 | 70 |
| Compression set, on O-rings ($\phi$ 25.4 × 3.53 mm):[5] | | | | |
| at 200° C. × 70 hours | 20 | 21 | 19 | 18 |
| at 200° C. × 168 hours | 32 | 31 | 32 | 30 |

[1]According to ASTM D 2705+68 T using an "oscillatingdisk rehometer" (biconical disk)
[2]According to ASTM D 1646-63, using a small-sized rotor
[3]According to ASTM D4 12-62 T on 2 mm thick test pieces
[4]According to ASTM D 14 15-68 on 6 mm thick test pieces; reading after 30 seconds
[5]According to ASTM D 395-61, method B.

EXAMPLE 2

Different vulcanization mixes were prepared, containing the polyoxidrylic vulcanizing agents indicated on Table 2. The accelerators $A_1$, $A_{12}$ and $A_{14}$ are those indicated in the previous example.

There was used the fluorinated elastomer known on the market under the name of Tecnoflon NL (trade mark by Montedison S.p.A. concerning an elastomeric copolymer of vinylidene fluoride with hexafluoropropene in a molar ratio of 4:1, with a Mooney ML (1+4) viscosity at 100° C.=45 and with a specific weight, at 25° C., equal to 1,816 g/cu.cm).

TABLE 2

| FORMULATION n° | 9 | 10 | 11 | 12 |
|---|---|---|---|---|
| Tecnoflon NL parts b.w. | 100 | 100 | 100 | 100 |
| Maglite D parts b.w. | 5 | 5 | 5 | 5 |
| Ca(OH)$_2$-VE[1] parts b.w. | 5 | 5 | 5 | 5 |
| Carbonblack MT parts b.w. | 30 | 30 | 30 | 30 |
| Bisphenol A parts b.w. | 2,3 | — | — | — |
| Bisphenol AF parts b.w. | — | 1,8 | — | — |
| Sulphondiphenol parts b.w. | — | — | 2,4 | — |
| Mono K 2-4-di-hydroxybenzophenone parts b.w. | — | — | — | 2,2 |
| $A_1$ parts b.w. | 0,6 | 0,6 | 0,65 | 0,8 |
| Thermo-mechanical characteristics: | | | | |
| O.D.R. 170° C. | | | | |
| Minimum torque in inch/lbs | 12 | 19 | 11 | 12 |
| $T_2$ in minutes[2] | 5,2 | 3 | 4,3 | 0,3 |
| $T_{50}$ in minutes[3] | 7,2 | 4,6 | 5,7 | 9,4 |
| Maximum torque in inch/lbs. | 86 | 120 | 95 | 85 |
| VISCOSITY: | | | | |
| Mooney MS at 121° C. minimum | 39 | 38 | 47 | 41 |
| minutes per increase of 10 points | 46 | +2 points after 50 minutes | +1 point after 50 minutes | 39 |
| VULCANIZATION: | | | | |
| on presses at 170° C. for 10 minutes | | | | |
| in an oven at 250° C. for 16 hours | | | | |
| Elastical modulus at 100% elongation Kg/sq.cm | 55 | 70 | 65 | 55 |
| Breaking load Kg/sq.cm | 130 | 165 | 140 | 135 |
| Elongation at break in % | 210 | 200 | 155 | 160 |
| Hardness, IRHD | 70 | 74 | 73 | 81 |
| Compression set, O-rings ($\phi$ 25.4 × 3.53 mm) | | | | |
| at 200° C. × 70 hours | 28 | 13 | 22 | 24 |
| at 200° C. × 168 hrs. | 40 | 23 | 39 | 35 |
| Thermol post-treatment: | | | | |
| at 275° C. × 70 hours | | | | |
| Variations in % of modulus 100% | +14 | 0 | +21 | +18 |
| Variations in % of breaking load | −21 | −18 | −14 | −15 |
| Variations in % of elongation | −19 | 0 | −4 | −12 |
| Variations of hardess, in points: | +2 | 0 | +1 | +3 |
| FORMULATION n° | 13 | 14 | 15 | 16 |
| Tecnoflon NL parts b.w. | 100 | 100 | 100 | 100 |
| Maglite D parts b.w. | 5 | 5 | 5 | 5 |
| Ca(OH)$_2$-VE[1] parts b.w. | 5 | 5 | 5 | 5 |
| Carbonblack MT parts b.w. | 30 | 30 | 30 | 30 |
| Bisphenol A parts b.w. | 2,3 | — | — | — |
| Bisphenol AF parts b.w. | — | 1,8 | — | — |
| Sulphondiphenol parts b.w. | — | — | 2,4 | — |
| Mono K 2-4-di-hydroxybenzophenone parts b.w. | — | — | — | 2,2 |
| $A_{12}$ parts b.w. | 0,5 | 0,5 | 0,55 | 0,75 |
| Thermo-mechanical characteristics: | | | | |
| O.D.R. 170° C. | | | | |
| Minimum torque in inch/lbs | 13 | 18 | 12 | 13 |

TABLE 2-continued

| | | | | |
|---|---|---|---|---|
| $T_2$ in minutes[2] | 5,5 | 3 | 5 | 6,5 |
| $T_{50}$ in minutes[3] | 7,5 | 4,4 | 6 | 9,1 |
| Maximum torque in inch/lbs. | 87 | 120 | 95 | 86 |
| VISCOSITY: | | | | |
| Mooney MS at 121° C. | | | | |
| minimum | 40 | 37 | 45 | 42 |
| minutes per increase of 10 points | 47 | +2 points after 50 minutes | +1 point after 50 minutes | 40 |
| VULCANIZATION: | | | | |
| on presses at 170° C. for 10 minutes | | | | |
| in an oven at 250° C. for 16 hours | | | | |
| Elastical modulus at 100% elongation Kg/sq.cm | 55 | 70 | 60 | 55 |
| Breaking load Kg/sq.cm | 125 | 160 | 145 | 140 |
| Elongation at break in % | 205 | 195 | 160 | 155 |
| Hardness, IRHD | 70 | 75 | 76 | 80 |
| Compression set, O-rings ($\phi$ 25.4 × 3.53 mm) | | | | |
| at 200° C. × 70 hours | 29 | 12 | 21 | 25 |
| at 200° C. × 168 hrs. | 40 | 23 | 40 | 33 |
| Thermal post-treatment: | | | | |
| at 275° C. × 70 hours | | | | |
| Variations in % of modulus 100% | +15 | 0 | +18 | +16 |
| Variations in % of breaking load | −20 | −16 | −14 | −14 |
| Variations in % of elongation | −18 | 0 | −3 | −11 |
| Variations of hardess, in points: | +3 | 0 | +1 | +2 |
| FORMULATION n° | 17 | 18 | 19 | 20 |
| Tecnoflon NL parts b.w. | 100 | 100 | 100 | 100 |
| Maglite D parts b.w. | 5 | 5 | 5 | 5 |
| Ca(OH)$_2$-VE[1] parts b.w. | 5 | 5 | 5 | 5 |
| Carbonblack MT parts b.w. | 30 | 30 | 30 | 30 |
| Bisphenol A parts b.w. | 2,3 | — | — | — |
| Bisphenol AF parts b.w. | — | 1,8 | — | — |
| Sulphondiphenol parts b.w. | — | — | 2,4 | — |
| Mono K 2-4-di-hydroxybenzophenone parts b.w. | — | — | — | 2,2 |
| A$_{14}$ parts b.w. | 0,5 | 0,5 | 0,55 | 0,7 |
| Thermo-mechanical characteristics: | | | | |
| O.D.R. 170° C. | | | | |
| Minimum torque in inch/lbs | 14 | 19 | 12 | 13 |
| $T_2$ in minutes[2] | 5 | 3,2 | 4,5 | 6,5 |
| $T_{50}$ in minutes[3] | 6,9 | 4,8 | 5,6 | 9,5 |
| Maximum torque in inch/lbs. | 90 | 115 | 95 | 90 |
| VISCOSITY: | | | | |
| Mooney MS at 121° C. | | | | |
| minimum | 39 | 38 | 46 | 41 |
| minutes per increase of 10 points | 47 | +2 points after 50 minutes | +1 point after 50 minutes | 40 |
| VULCANIZATION: | | | | |
| on presses at 170° C. for 10 minutes | | | | |
| in an oven at 250° C. for 16 hours | | | | |
| Elastical modulus at 100% elongation Kg/sq.cm | 55 | 65 | 65 | 60 |
| Breaking load Kg/sq.cm | 130 | 160 | 140 | 140 |
| Elongation at break in % | 210 | 195 | 160 | 155 |
| Hardness, IRHD | 70 | 75 | 72 | 80 |
| Compression set, O-rings ($\phi$ 25.4 × 3.53 mm) | | | | |
| at 200° C. × 70 hours | 29 | 14 | 21 | 22 |
| at 200° C. × 168 hrs. | 41 | 22 | 38 | 32 |
| Thermal post-treatment: | | | | |
| at 275° C. × 70 hours | | | | |
| Variations in % of modulus 100% | +43 | +5 | +20 | +15 |
| Variations in % of breaking load | −20 | −16 | −12 | −15 |
| Variations in % of elongation | −17 | −5 | −4 | −12 |
| Variations of hardness, in points: | +3 | 0 | +1 | +2 |

[1]Trade Mark OF STURGE Ltd. (England)
[2]Time in minutes necessary for the increase of the minimum value 2 inch/lbs.
[3]Time in minutes necessary for getting a torque of 50 inch/lbs.

EXAMPLE 3

In this instance there was used bisphenol AF as a vulcanizing agent and the following compounds as accelerators:

$A_5 = P[N(CH_3)_2]_3 (CH_2C_6H_5) Cl$
$A_6 = P[N(CH_3)_2]_3 (2-ClC_6H_4CH_2) Cl$
$A_7 = P[N(C_2H_5)_2]_3 (C_6H_5CH_2) PF_6$
$A_8 = P[N(C_2H_5)_2]_3 (CH_3) I$
$A_9 = P[N(C_2H_5)_2]_2 (C_6H_5) (C_6H_5CH_2) BF_4$
$A_{12}$ = as in example 1
$A_{13}$ = as in example 1
$A_{14}$ = as in example 1
$A_{15}$ = as in example 1

The formulations and results therefrom obtained have been recorded on Table n° 3.

TABLE 3

| FORMULATIONS n° | 21 | 22 | 23 | 24 | 25 |
|---|---|---|---|---|---|
| Tecnoflon NM parts b.w. | 100 | 100 | 100 | 100 | 100 |
| Maglite D parts b.w. | 3 | 3 | 3 | 3 | 3 |
| Ca(OH)$_2$-VE (*) parts b.w. | 6 | 6 | 6 | 6 | 6 |
| Carbonblack MT parts b.w. | 25 | 25 | 25 | 25 | 25 |
| Bisphenol AF parts b.w. | 1,6 | 1,6 | 1,6 | 1,6 | 1,6 |
| A$_5$ parts b.w. | 0,4 | — | — | — | — |
| A$_6$ parts b.w. | — | 0,6 | — | — | — |
| A$_7$ parts b.w. | — | — | — | 0,7 | — |
| A$_8$ parts b.w. | — | — | 0,5 | — | — |
| A$_9$ parts b.w. | — | — | — | — | 0,6 |
| Thermo-mechanical characteristics | | | | | |
| O.D.R. 170° C. | | | | | |
| Minimum torque in inch/lbs. | 21 | 20 | 17 | 22 | 23 |
| T$_2$ minutes | 3,8 | 3,6 | 3,1 | 2,5 | 3,4 |
| T$_{50}$ minutes | 4,9 | 4,1 | 4,6 | 3,1 | 5,2 |
| Maximum torque in inch/lbs. | 100 | 115 | 105 | 120 | 120 |
| VISCOSITY | | | | | |
| Mooney MS at 121° C. | | | | | |
| minimum | 58 | 51 | 50 | 49 | 50 |
| minutes for 10 pint increase | 45 | +1 point after 58 minutes | +4 points after 50 minutes | 44 | 45 |
| VULCANIZATION: | | | | | |
| on press at 170° C. × 10 minutes | | | | | |
| on oven at 250° C. × 15 hours | | | | | |
| Elastical modulus at 100% of elong. Kg/sq.cm | 55 | 65 | 65 | 70 | 70 |
| Breaking load Kg/sq.cm | 155 | 160 | 145 | 140 | 145 |
| Elongation at break in % | 215 | 200 | 195 | 160 | 165 |
| Hardness, IRHD | 66 | 67 | 69 | 65 | 68 |
| Compression set, O-rings (φ 25,4 × 3,53 mm) | | | | | |
| at 200° C. for 70 hours | 16 | 17 | 15 | 18 | 18 |
| at 200° C. for 336 hrs. | 40 | 42 | 33 | 38 | 41 |

| FORMULATIONS n° | 26 | 27 | 28 | 29 |
|---|---|---|---|---|
| Tecnoflon NM parts b.w. | 100 | 100 | 100 | 100 |
| Maglite D parts b.w. | 3 | 3 | 3 | 3 |
| Ca(OH)$_2$-VE (*) parts b.w. | 6 | 6 | 6 | 6 |
| Carbonblack MT parts b.w. | 25 | 25 | 25 | 25 |
| Bisphenol AF parts b.w. | 1,6 | 1,6 | 1,6 | 1,6 |
| A$_{12}$ parts b.w. | 0,4 | — | — | — |
| A$_{13}$ parts b.w. | — | 0,45 | — | — |
| A$_{14}$ parts b.w. | — | — | 0,4 | — |
| A$_{15}$ parts b.w. | — | — | — | 0,4 |
| Thermo-mechanical characteristics | | | | |
| O.D.R. 170° C. | | | | |
| Minimum torque in inch/lbs. | 21 | 20 | 19 | 21 |
| T$_2$ minutes | 3,7 | 2,9 | 3,7 | 3,6 |
| T$_{50}$ minutes | 4,8 | 4,1 | 5,1 | 5,2 |
| Maximum torque in inch/lbs. | 115 | 120 | 115 | 120 |
| VISCOSITY | | | | |
| Mooney MS at 121° C. | | | | |
| minimum | 50 | 51 | 49 | 51 |
| minutes for 10 pint increase | 45 | 45 | 44 | 44 |
| VULCANIZATION: | | | | |
| on press at 170° C. × 10 minutes | | | | |
| on oven at 250° C. × 16 hours | | | | |
| Elastical modulus at 100% of elong. Kg/sq.cm | 65 | 70 | 65 | 70 |
| Breaking load Kg/sq.cm | 150 | 155 | 165 | 165 |
| Elongation at break in % | 180 | 195 | 200 | 205 |
| Hardness, IRHD | 67 | 68 | 69 | 67 |
| Compression set, O-rings (φ 25,4 × 3,53 mm) | | | | |
| at 200° C. for 70 hours | 20 | 21 | 18 | 18 |
| at 200° C. for 336 hrs. | 39 | 40 | 39 | 37 |

(*)Trade mark of STURGE Ltd. (England).

EXAMPLE 4

2.6 mm thick "O" rings of 20 g each, were injection molded according to the formulations reported on Table 4. The molding die for the "O" rings had 16 impressions. The accelerators used in the mix were the following:

$A_1$, $A_4$, $A_{12}$, $A_{14}$, $A_{15}$: as specified in example 1
$A_{10}$ = N-metoxy, N-methyl-piperidinium iodide
$A_{11}$ = n.propyl-tributyl-ammonium iodide.

At the usual plasticizing temperatures, with the accelerators $A_{10}$ and $A_{11}$ of the Prior Art, difficulties are met in the injection because of the "scorching" phenomenon.

Lowering the plasticizing temperature, the injection times become too long and there appear stickiness and tearing phenomena under the heat.

proves to be that of seals on rotating shafts achieved by means of oil retainer or oil seal rings.

In this case it is indispensable that between the elastomeric part and the metal insert there be a perfect adhesion, resisting even to high temperatures (200°–250° C.). The adhesion is achieved during the vulcanization stage in the press, using the adhesive Chemosil 510 (*), trade mark product of Henkel, a liquid product which is spread on the test piece beforehand.

It is necessary that there be a perfect balance between the vulcanization speed of the mix and the action of the attack agent.

In the case of too high a vulcanization speed, the elastomeric part reticulates within a very short time, before the adhesive exerts its action. In such a case there occurs the complete coming off the elastomeric part from the metal insert. It is therefore absolutely neces-

TABLE 4

| FORMULATIONS n° | 30 | 31 | 32 | 33 |
|---|---|---|---|---|
| Tecnoflon NM parts. b.w. | 100 | 100 | 100 | 100 |
| Maglite D parts b.w. | 5 | 5 | 5 | 5 |
| Ca(OH)$_2$-VE (*) parts b.w. | 5 | 5 | 5 | 5 |
| Carbonblack MT parts b.w. | 25 | 25 | 25 | 25 |
| Polyethylene AC/6 17A[1] parts b.w. | 1 | 1 | 1 | 1 |
| Carbauba wax parts b.w. | 1 | 1 | 1 | 1 |
| Bisphenol AF parts b.w. | 1.65 | 1.65 | 1.65 | 1.65 |
| $A_1$ parts b.w. | 0.5 | — | — | — |
| $A_4$ parts b.w. | — | 0.45 | — | — |
| $A_{10}$ parts b.w. | — | — | 0.85 | — |
| $A_{11}$ parts b.w. | — | — | — | 0.65 |
| Plasticizing temperature at 95° C. | | | | no injection because of scorching |
| Injection time | 1 sec. | 1.5 sec. | 3 sec. | |
| Temperature of mold 200° C., Vuclanization time | 19 sec. | 21 sec. | 20 sec. articles w. scorching marks | |
| Plastizing temperature at 70° C. - Injection time | 2 sec. | 3 sec. | 12 sec. | 18 sec. |
| Mold temperature at 90° C. - Vulcanization time | 29 sec. | 51 sec. | 31 sec. | 35 sec. articles w. scorching marks easily subject to tearings |

| FORMULATIONS n° | 34 | 35 | 36 |
|---|---|---|---|
| Tecnoflon NM parts. b.w. | 100 | 100 | 100 |
| Maglite D parts b.w. | 5 | 5 | 5 |
| Ca(OH)$_2$-VE (*) parts b.w. | 5 | 5 | 5 |
| Carbonblack MT parts b.w. | 25 | 25 | 25 |
| Polyethylene AC/6 17A[1] parts b.w. | 1 | 1 | 1 |
| Carbauba wax parts b.w. | 1 | 1 | 1 |
| Bisphenol AF parts b.w. | 1.65 | 1.65 | 1.65 |
| $A_{12}$ parts b.w. | 0.4 | — | — |
| $A_{14}$ parts b.w. | — | 0.45 | — |
| $A_{15}$ parts b.w. | — | — | 0.45 |
| Plasticizing temperature at 95° C. Injection time | 1.5 sec. | 1.5 sec. | 1 sec. |
| Temperature of mold 200° C., Vuclanization time | .18 sec. | 27 sec. | 20 sec. |
| Plastizing temperature at 70° C. - Injection time | 3 sec. | 3 sec. | 2 sec. |
| Mold temperature at 90° C. - Vulcanization time | 35 sec. | 40 sec. | 42 sec. |

(*) Trade mark of STURGE Ltd. (England)
[1]Polyethylene produced by ALLIED

EXAMPLE 5

As is well known, one of the most wide-spread applications of fluorinated elastomers is to be found in the field of gaskets for both statical as well as dynamical sealing. Under this aspect, a particularly important field sary that the action of the accelerator develops in perfect concomittance with that of the adhesive. In other words, the vulcanization curve should show a not completely vertically upwards rising graph, so that from the minimum value to the maximum value there shall laps a certain stretch of time (3–9 minutes).

This requirement is completely satisfied by the accelerators of this invention.

On Table 5 there have been recorded the values of the adhesive force, values that have been determined by means of an AMSLER dynamometer, for formulations of Tecnoflon containing accelerators $A_1$ and $A_4$ according to this invention (formulations 37 and 38), already indicated in example no. 1, and for comparative purposes, those obtained by using an accelerator of the Prior Art, of the type of quaternary ammonium salt (formulation 39) which exerts a pronounced accelerating action.

TABLE 5

| RUBBER/metal adhesion values (ASTM D 429-68 TRT. B - (DEG 9) for some vulcanizable compositions: | | | |
|---|---|---|---|
| FORMUATIONS n° | 37 | 38 | 39 |
| Tecnoflon NM parts b.w. | 100 | 100 | 100 |
| Maglite D parts b.w. | 5 | 5 | 5 |
| Ca(OH)$_2$ parts b.w. | 5 | 5 | 5 |
| Carbonblack MT parts b.w. | 30 | 30 | 30 |
| Bisphenol AF parts b.w. | 1.6 | 1.6 | 1.6 |
| A$_1$ parts b.w. | 0.5 | — | — |
| A$_4$ parts b.w. | — | 0.5 | — |
| Tetrabutylammonium 1 parts b.w. | — | — | 0.6 |
| Adhesive force Kg/sq.cm | | | |
| After vulcanization on press at 175° C. for 12 minutes | 9* | 7.6* | 3 |
| After post-vulcanization in an oven at 200° C. for 24 hours | 6.6* | 4.9* | — |
| After thermal aging at 250° C. for 7 days | 4.2* | 4* | — |

*The values found and herein above recorded shall not be considered "effective" in as much as they do not refer to phenomena of a "clean breakaway", but do refer to tearing and breaking phenomena of the elastomeric part. This explains the fact that the adhesion value decreases when passing from vulcanization at 180° C. under pressure to a vulcanization at 250° C. in an oven, up to the heat treatment at 250° C. for 7 days just because the brittleness of the fluorinated elastomer is directly proportional to the degree of vulcanization attained which in its turn depends directly from the temperature and the time of treatment.

We claim:

1. Vulcanizable compositions consisting of:

(I) 100 parts by weight of an elastomeric copolymer of vinylidene fluoride, with at least one fluorinated or chlorofluorinated, ethylenically unsaturated monomer;

(II) 1–40 parts by weight of an acceptor of inorganic acid, consisting of at least one basic oxide of a bivalent metal, selected from the group consisting of magnesium oxide, calcium oxide, lead monooxide, zinc oxide and/or at least one basic lead phosphite;

(III) 0.5–10 parts by weight of at least one basic compound selected from the group consisting of calcium, strontium, barium, sodium and potassium phosphates;

(IV) 0.5–15 parts by weight of a vulcanizing agent based on at least one polyhydroxyl and/or polythiol compound of general formulae:

$$A(XZ)_n \text{ and/or } ZX—R—XZ$$

wherein A is an arylene radical; n is a whole number equal to at least 2; X is oxygen or sulphur; Z is hydrogen or an alkaline metal; R is an alkylene, cycloalkylene, mono- or polyalkylencycloalkyl, alkylendiaryl or oxoalkylendiaryl radical; and (V) 0.05–5 parts by weight of a vulcanization accelerator which is an aminophosphinic derivative of the general formulae:

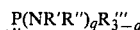
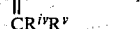
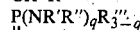
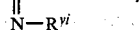

wherein:

R', R" and R''', the same or different, are alkyl, cycloalkyl, aryl, arylalkyl, oxyalkyl or polyoxyalkyl groups having a free or etherified terminal OH function and containing from 1 to 18 carbon atoms; such an alkyl, cycloalkyl, aryl, arylalkyl, oxyalkyl or polyoxyalkyl group substituted by halogen, CN, OH or carbalkoxy; or such alkyl, cycloalkyl, aryl, arylalkyl, oxyalkyl or polyoxyalkyl groups in which R' and R" together form, with the nitrogen atom, a heterocyclic ring;

q is a whole number comprised between 1 and 3;

$R^{iv}$ is hydrogen, an alkyl group containing from 1 to 16 carbon atoms, or a carbalkoxy group —COOR in which R is a $C_1$–$C_8$ alkyl;

$R^v$ is a carbalkoxy group —COOR in which R is a $C_1$–$C_8$ alkyl, the —CN group, the —CONH$_2$ group, a $C_1$–$C_{16}$ alkyl group, or an aryl group; or $R^{iv}$ and $R^v$ form, with the carbon atom, the cyclic group

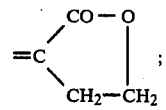

$R^{vi}$ is an aryl group, a carbalkoxy group —COOR in which R is a $C_1$–$C_8$ alkyl, a carbaryloxy group —COOAr in which Ar is aryl; or $R^{vi}$ is an ionic group having one of the formulae:

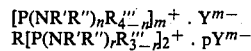
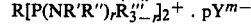

wherein:

R', R", R''' have the same meanings as in formulae (I) and (II);

R is a bivalent alkylenic, arylenic or oxoalkylenic radical;

n is a whole number comprised between 1 and 4;

r is a whole number comprised between 1 and 3;

m is a whole number comprised between 1 and 3, corresponding to the valence of anion Y;

m.p. = 2, and

Y is an organic or inorganic anion of valency m.

2. Vulcanizable compositions according to claim 1, characterized in that the vulcanization accelerator (V) consists of (I), (II), (III) or (IV) in which:

$R^{iv}$ is H or CH$_3$, $R^v$ is —COOCH$_3$ or —COOC$_2$H$_5$;

$R^{vi}$ is —C$_6$H$_5$ or —C$_6$H$_4$CH$_3$;

R''' is alkylaryl or alkyl with from 1 to 6 carbon atoms;

R' and R" are methyl or ethyl;

q = 2 or 3 in formula (I) and 3 in formula (II);

Y is Cl$^-$, Br$^-$, I$^-$, HgI$_4^{--}$, or CdCl$_4^{--}$.

3. Vulcanizable compositions according to claim 1, in which the fluorinated or chlorofluorinated, ethylenically unsaturated monomer is selected from the group consisting of 1-hydropentafluoropropene, 2-hydropentafluoropropene, 1,1-dihydrotetrafluoropropene, hexafluoropropene, tetrafluoroethylene, trifluorochloroethylene, fluoroalkyl ethers and fluoroarylvinyl ethers.

4. Vulcanizable compositions according to claim 1, in which the inorganic acid acceptor (II) is in the form of a complex or cationic chelate.

5. Vulcanizable compositions according to claim 1, in which the basic compound (III) is complexed with a complexing or cationic chelating agent.

6. Vulcanizable compositions according to claim 2, further characterized in that, in the vulcanization accelerator, R''' is benzyl.

7. Vulcanizable compositions according to claim 1, in which, in the vulcanization accelerator (V), the alkyl, cycloalkyl, aryl, arylalkyl, oxyalkyl or polyoxyalkyl groups R', R'' and R''' have from 1 to 12 carbon atoms.

* * * * *